(12) United States Patent
Saavedra

(10) Patent No.: US 6,261,308 B1
(45) Date of Patent: Jul. 17, 2001

(54) MEDICAL FORCEPS FOR VASCULAR SURGERY

(76) Inventor: Carlos A. Saavedra, 4868 Stonehedge Dr., Akron, OH (US) 44333

( * ) Notice: Subject to any disclaimer, the term of this patent is extended or adjusted under 35 U.S.C. 154(b) by 0 days.

(21) Appl. No.: 09/370,134

(22) Filed: Aug. 9, 1999

(51) Int. Cl.[7] .................................................. A61B 17/28
(52) U.S. Cl. ......................................... 606/207; 606/158
(58) Field of Search ................................... 606/205, 207, 606/158, 151, 157, 210; 81/419, 420; 600/219

(56) References Cited

U.S. PATENT DOCUMENTS

| | | | |
|---|---|---|---|
| 4,803,983 | * | 2/1989 | Siegel .................................... 128/321 |
| 5,891,017 | * | 4/1999 | Swindle et al. ....................... 606/205 |
| 5,891,162 | * | 4/1999 | Sugarbaker et al. .................. 606/207 |
| 6,007,552 | * | 12/1999 | Fogarty et al. ....................... 606/207 |

* cited by examiner

*Primary Examiner*—Michael H. Thaler
*Assistant Examiner*—Anthony S. King
(74) *Attorney, Agent, or Firm*—Renner, Kenner, Greive, Bobak, Taylor & Weber

(57) ABSTRACT

Medical forceps for vascular surgery are presented. The forceps serve as vascular clamps, allowing a vascular surgeon to close torn or ruptured veins, both laterally and transversely, and to allow the clamp to remain in place without damaging the veins. The forceps are constructed of flexible stainless steel stems, having a two clamps defined at one end thereof in the form of interengaging rows of teeth. At an opposite end of the stems, a pair of grips are presented for use by the surgeon. Maintained in close proximity to the grips are a pair of locking tabs, one associated with each of the stems, the locking tabs being configured to allow for selective locking engagement of either of the clamps defined at the opposite end of the forceps. The forceps are preferably manufactured of 420 stainless steel, appropriately heat treated such that the flexibility of the stems dissipates much of the force imparted through the grips, such that a clamped vein is not damaged thereby.

7 Claims, 3 Drawing Sheets

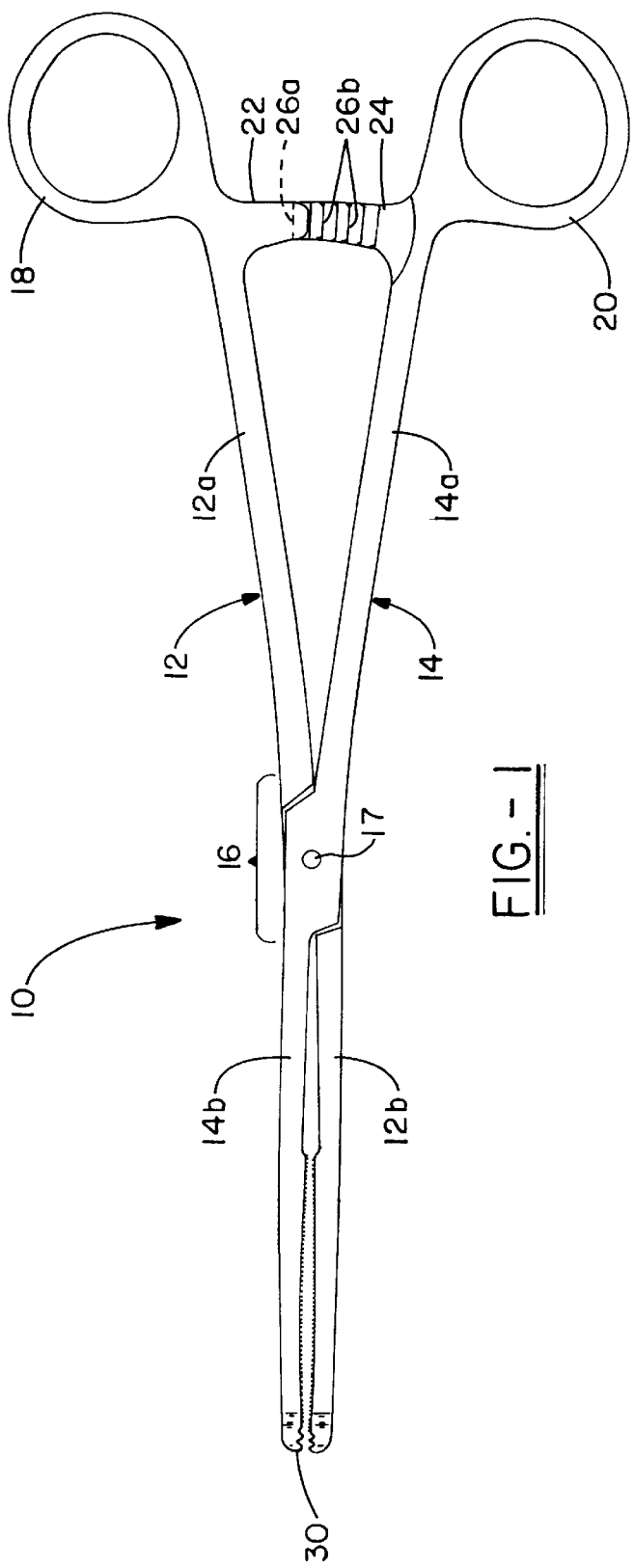
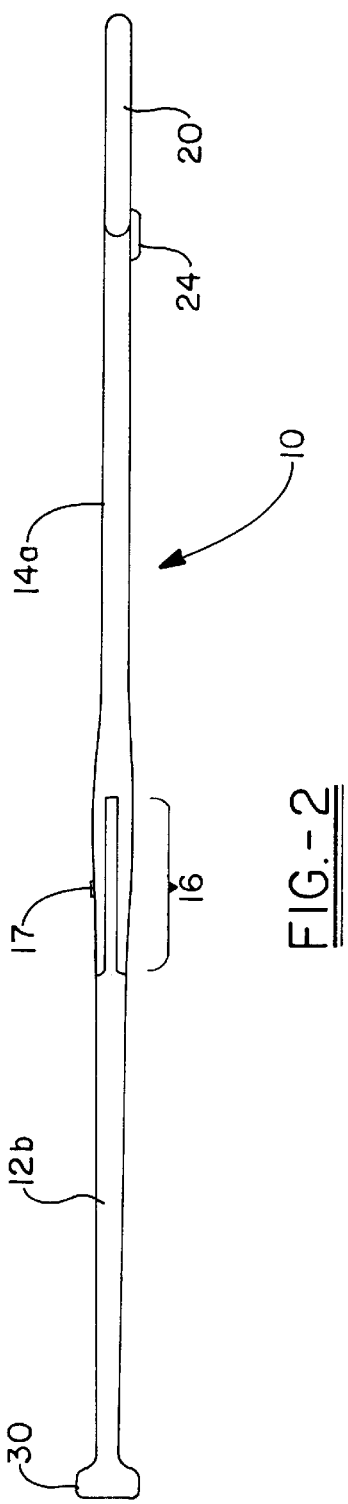

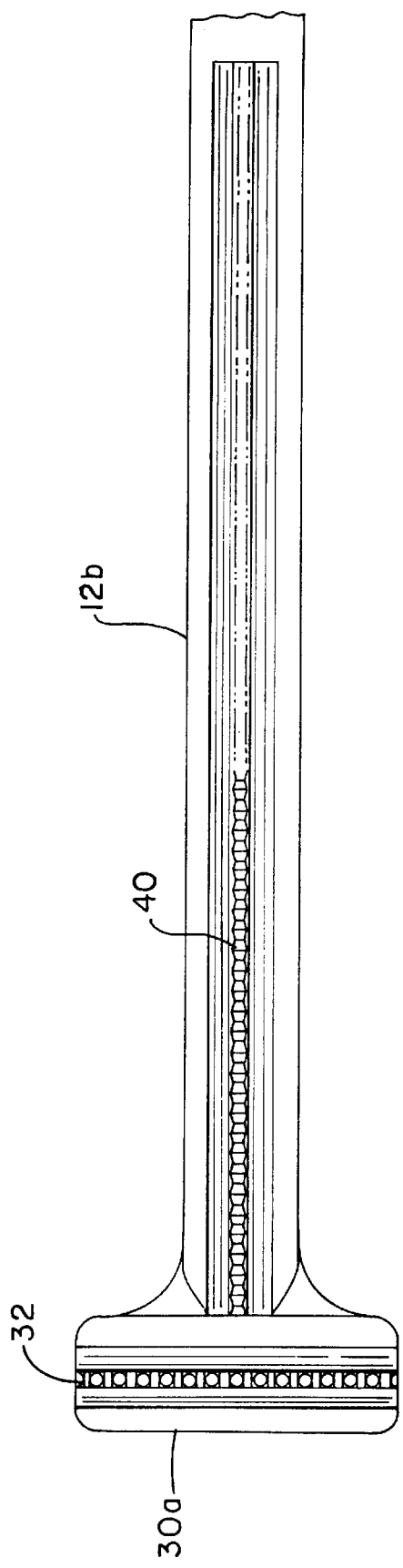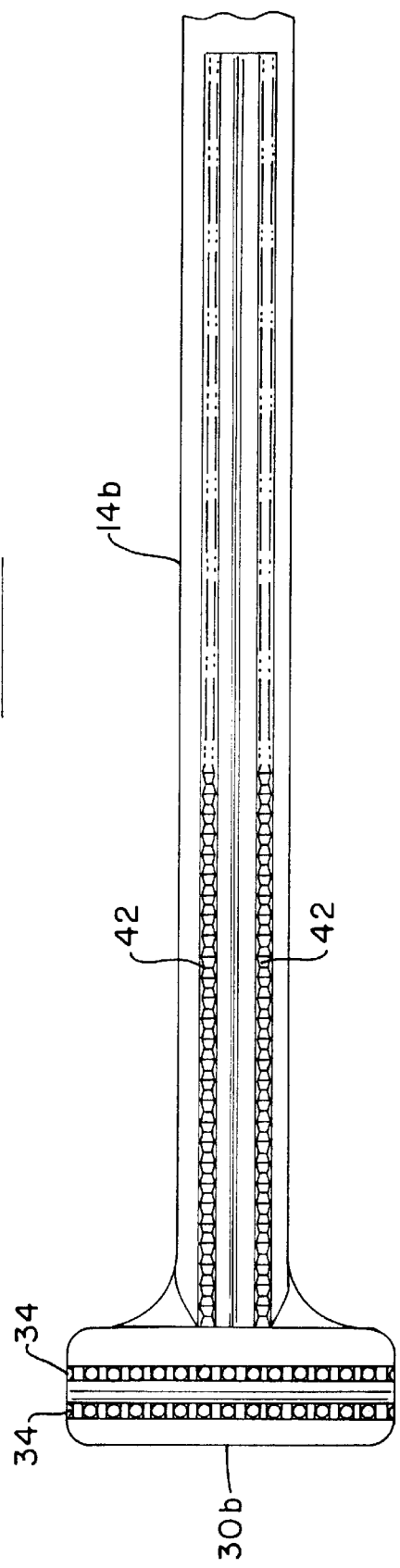

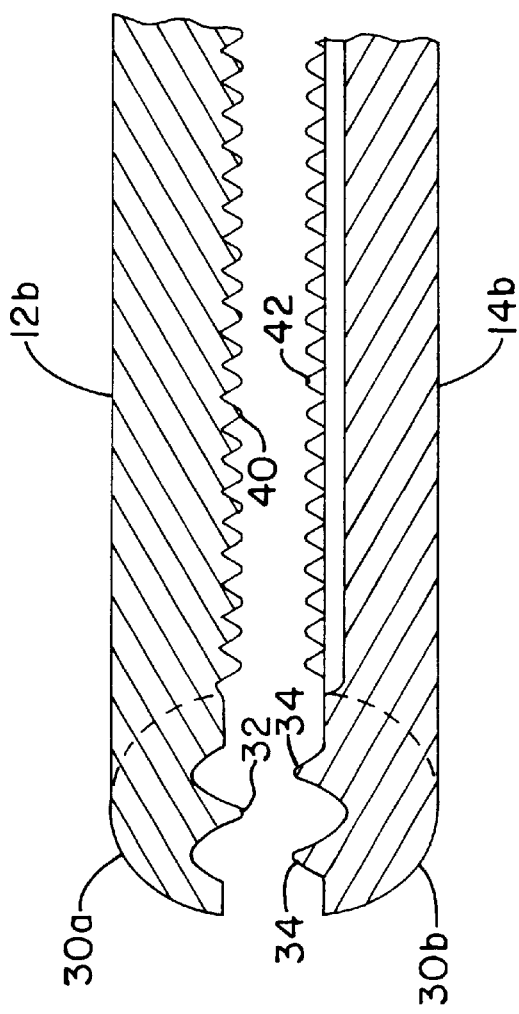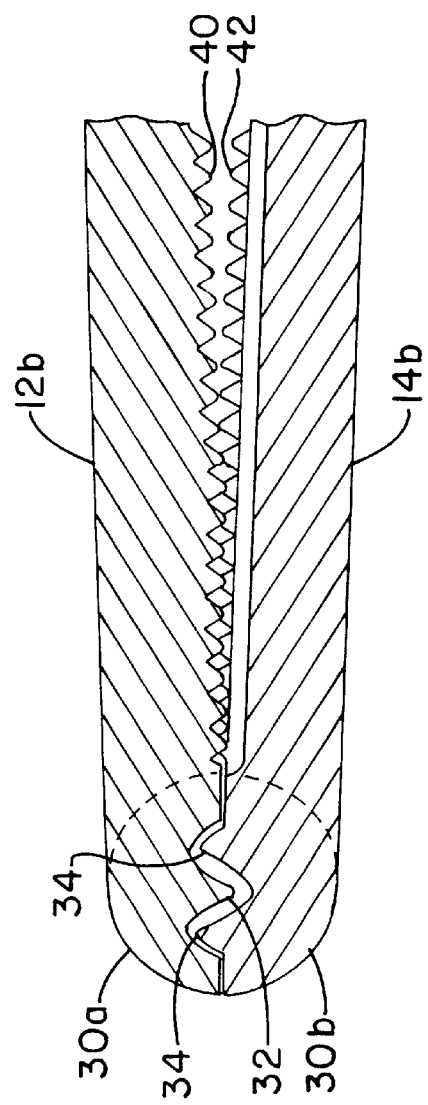

MEDICAL FORCEPS FOR VASCULAR SURGERY

TECHNICAL FIELD

The present invention relates generally to medical forceps. More particularly, the present invention relates to medical forceps for vascular surgery, the forceps being made of vascular steel to provide a vascular surgeon with the ability to cross clamp and/or sequentially side clamp a damaged vein without puncturing, tearing or otherwise damaging the vein.

BACKGROUND ART

In their profession, vascular surgeons must quickly locate and repair damaged veins. Many times these veins are of substantial size, and patients with a torn, severed, or burst vein may suffer substantial vital blood loss before the veins can be repaired if the flow of blood out of the damaged vein is not substantially lessened while the surgeon operates.

Therefore, vascular surgeons and their assistants typically control the blood loss from damaged veins by local pressure and/or cross clamping the injured vessel on both sides of the damages area to allow definite repair of the injured vessel.

Proximal and distal control of the inured vein may not be possible or effective in patents with presence of massive hemorrhage such as injuries located in an area of major veins confluence such as interior vena cava bifurcation, suprarenal retrohepatic vena cava, portal vein confluence, and the like.

It has been discovered, as will become apparent hereinbelow, that the novel medical forceps of the invention may be used to effectively control catastrophic hemorrhage from laceration of a substantial size vein when other methods or clamps could not be used or are ineffective. In these circumstances, with digital compression and sequential application of this novel clamp the threatening hemorrhage is controlled and definite repair of the injured vein is possible. This novel clamp allows the vascular surgeon to cross clamp the vessel when needed or feasible, while also allowing for sequential side clamping of injured undissected vessels without proximal and distal control.

In sequential side clamping the vein opening is clamped shut by a series of medical forceps clamped side by side along the opening of the vein. This method clamps only the portion of the vein that is torn, punctured or cut and operates to close the opening, while cross clamping stems the flood of blood into the damaged area by clamping the entire width of the vein. The sequential side clamping is more appropriately used when an axial tear is present along a portion of the vein. Medical forceps of the prior art do not provide adequate means for sequential side venous closure. Such prior art medical forceps, when used during vascular surgery, provide a bite which is too sharp or harsh, and therefore tend to puncture or tear the vein to which they are clamped.

Thus there exists the need for a means for temporary closure and stemming the flow of blood through a damaged vein of substantial size, without causing further damage to the vein or adjacent vital organs, in order to aid the vascular surgeon in operating on the controlling massive life threatening hemorrhage, and repairing a torn, severed, punctured or burst vein unable to be controlled by other means.

DISCLOSURE OF INVENTION

In light of the foregoing, it is an object of the present invention to provide a medical forceps for venous closure which can be used to effect a cross clamp or a sequential side clamp.

It is another object of the present invention to provide a medical forceps for venous closure that will hold the vein in a substantially permanent, secure grip so as to remain in place during the operation without the aid of a vascular surgeon.

It is still another object of the present invention to provide a medical forceps for venous closure which, when clamped onto a vein, does not bring about the undesired effect of biting sharply into the vein so as to puncture, tear, or otherwise damage the vein.

The foregoing and other aspects of the invention which will become apparent as the detailed description proceeds are achieved by medical forceps for vascular surgery, comprising: a first flexible stem; a second flexible stem pivotally connected to said first flexible stem; first and second grips respectively maintained at first ends of each of said first and second stems; first and second tips respectively maintained at second ends of each of said first and second stems, said first and second tips defining a first vascular clamp; and a selectably actuatable and releasable lock interposed between said first and second flexible stems.

BRIEF DESCRIPTION OF THE DRAWINGS

For a complete understanding of the objects, techniques and structure of the invention, reference should be made to the following detailed description and accompanying drawings wherein:

FIG. 1 is an elevational view of a configuration for the medical forceps of the present invention;

FIG. 2 is an edge view of the medical forceps of the present invention;

FIG. 3 is an enlarged view of the inside surface of one of the jaws of the medical forceps of the present invention;

FIG. 4 is an enlarged view of the inside surface of the opposite jaw of FIG. 3 of the medical forceps of the present invention;

FIG. 5 is an enlarged side view, in cross-section through the center lines of both jaws, illustrating teeth configurations on the inside surface of the jaws; and FIG. 6 is an enlarged side view, in cross-section through the centerline of both jaws, illustrating engagement of the jaws.

BEST MODE FOR CARRYING OUT THE INVENTION

Referring now to FIG. 1, it can be seen that the medical forceps of the present invention is shown and designated generally by the numeral 10. The medical forceps 10 has a flexible stem 12 which is interconnected with and substantially similar to a flexible stem 14. Stems 12 and 14 are of one piece construction and each has a handle 12a and 14a and jaw 12b and 14b and are pivotally connected at yoke 16. Handles 12a and 14a bow outwardly from yoke 16 as the handles increase in length from yoke 16 toward thumb grip 18 and finger grip 20 so that, in a closed position as shown in FIG. 1, the distance between handles 12a and 14a increases as the handles 12a and 14a extend from yoke 16 toward grips 18 and 20.

It should be noted here, and appreciated throughout the disclosure hereinbelow, that the medical forceps 10 is substantially axially symmetrical. Therefore, it will be realized by those of ordinary skill in the art that descriptions attributing features to a certain portion of the stem 12 or 14 of the medical forceps 10 may be, instead, attributed to the symmetrically related portion of the opposing stem without deviating from the scope of the present invention.

Handles 12a and 14a lie on the same plane and are provided with locking tabs 22 and 24, respectively, which extend along that plane and generally toward such other in the direction of the area between handles 12a and 14a. Tabs 22 and 24 are slightly offset so that locking tab 22 passes over locking tab 24 as stems 12 and 14 are squeezed more closely together by exerting force on grips 18 and 20 in the direction of tabs 22 and 24. Ribs 26a, provided on the inner surface of locking tab 22, and ribs 26b, provided on the inner surface of locking tab 24, extend from their respective tabs so that ribs 26a and 26b rub over each other as tabs 22 and 24 pass each other during closure of handles 12a and 14a. The shape of ribs 26a and 26b is such that they allow for closure of the space between handles 12a and 14a but releasably lockingly mate at intervals thereby resisting opening and effecting a lock of the position of the stems 12 and 14.

This interlocking is achieved by ribs 26a, 26b being shaped similar to a right triangle so that, as handles 12a and 14a are brought closer together, the hypotenuse of each rib on a locking tab pushes against the hypotenuse of each opposing rib on the opposing locking tab, thereby distending tabs 22 and 24 away from each other until the right angles of the ribs align at which time the ribs 26a and 26b of tabs 22 and 24 forcibly engage from their distended position and closure of stems 12 and 14 is locked in place. It should be appreciated that the multitude of ribs provided on tabs 22 and 24 can lock along the entire length of the tabs 22 and 24 and, as the number of interlocking ribs increases, the force of the closure created also increases. It will be appreciated that the number and resultant spacing of the ribs 26a and 26b establishes the incremental graduation of the closure force or bite available to the user. Furthermore, while the ribs 26a and 26b herein disclosed for purposes of the preferred embodiment are similar in shape to a right triangle, thereby establishing a plurality of ramped teeth adapted for selective interengagement with each other, other forms of mating ribs may be employed while falling within the scope of the present invention.

As mentioned above, and seen more particularly in FIG. 2, stems 12 and 14 are interconnected at yoke 16. At yoke 16, one stem is received in a yoke provided by the other stem and secured by a pivot pin 17. Stems 12 and 14 cross at this point so that, as shown in FIG. 1, the jaw 12b of stem 12 lies below jaw 14b of stem 14, whereas handle 12a lies above handle 14a. Thus, movement of handle 12a away from 14a will cause jaw 12b to move away from jaw 14b and vice versa. Handle 14a and jaw 14b also move in this manner. Therefore, an increase in the distance between handles 12a and 14a or, to state it more simply, opening handles 12a and 14a, causes jaws 14b and 12b to open, while closing handles 12a and 14a causes jaws 12b and 14b to close.

When closing, jaws 12b and 14b will first intimately meet at broad tip 30. Preferably, jaws 12b and 14b intimately meet at broad tip 30 before ribs 26a and 26b come into contact so that the medical forceps 10 may be used without necessarily engaging ribs 26a and 26b and locking up the forceps.

With further attention to FIG. 1, it can be seen that jaws 12b and 14b bow slightly away from each other so that, when not tightly closed, they only intimately contact each other at broad tip 30. As greater closure force is exerted through grips 18 and 20, the space between jaws 12b and 14b becomes smaller and the surface area in contact becomes larger. Ribs 26a and 26b serve to lock this area of contact into place and resist the tendency of jaws 12b and 14b to bow away from one another. In the fully clamped position, wherein the entire length of tab 22 is engaged with tab 24, the greatest clamping effect is created between the inner surface of jaws 12b and 14b and they intimately contact one another along substantially the entire length of the bowed portion.

Referring now to FIGS. 3 and 4, it can be seen that the inner surface of jaw 12b has a row of teeth 40 while the inner surface of jaw 14b has two spaced apart parallel rows of teeth 42. As stated hereinabove, it should be appreciated that positioning of the single row of teeth 40 and the two rows of teeth 42 may be reversed inasmuch as the medical forceps 10 is a substantially axially symmetrical device. The single row of teeth 40 is received within the area between the two rows of teeth 42 when substantial closure of handles 12a and 14a bring about intimate contact between the inner surface of jaws 12b and 14b. The rows of teeth 40, 42 may extend along any desired length of the jaws 12b, 14b between the tip 30 and yoke 16, typically ending within about 1 cm of the yoke 16.

It should be noted that the teeth 40, 42 are generally triangular in shape to provide a grip onto the vascular tissue and the peaks and valleys created by the teeth 40 and 42 do not intimately mate. Indeed, with the row of teeth 40 being received between the rows of teeth 42, there is no mating of teeth at all. However, when performing a cross clamp procedure on a vein, this arrangement causes the vein to be pinched closed in a serpentine manner, with the teeth 40, 42 preventing the forceps 10 from disengaging the vein. Preferably, the teeth 40, 42 are of the type employed in ATRAUGRIP® jaws as made and sold by Pilling Weck of Fort Washington, Pa.

As seen in FIGS. 2, 3 and 4, the tips of jaws 12b and 14b are uniquely broaden in a direction perpendicular to jaws 12b and 14b to provide a more substantial surface area of contact thereat. Tip 30a of jaw 12b is provided with a single row of teeth 32 while tip 30b of jaw 14b is provided with two rows of teeth 34, with both sets of teeth 32 and 34 running perpendicular to teeth 40 and 42. Teeth 32 and 34 are shaped and work in the same manner as teeth 40 and 42; however, the clamp of tips 30a, 30b is normally used for sequential side clamping. Again, the teeth 32, 34 are preferably those employed in ATRAUGRIP® jaws made and sold by Pilling Weck.

As shown in FIGS. 5 and 6, the row of teeth 32 is positioned to be received between the parallel rows of teeth 34, respectively positioned on the inner faces of tips 30a and 30b of jaws 12b and 14b. The nature of the teeth 32, 34 is well known and understood by those skilled in the art and are widely accepted for being gentle to tissue. Such teeth, when employed in the structure presented herein, have also been found to be sufficiently gentle to veins to allow for sealing clamping engagement without damage. In this regard, the pivotally connected stems 12, 14 must be sufficiently flexible that a reduced portion of force applied at the grips 18, 20 translates into force at the bite created at teeth 32, 34 and 40, 42. In other words, a portion of the force applied at the grips 18, 20 is dissipated or relieved by the flexibility of the handles 12a, 14a and jaws 12b, 14b such that a reduced force is applied to the vein itself. That force, however, has been found to be sufficient to close veins without damage, and to allow the forceps 10 to remain lockingly engaged to the vein once the locking tabs 22, 24 are engaged as by the ribs 26a, 26b. It has been found that desired flexibility may be imparted to the handles and jaws as aforesaid by employing 420 stainless steel appropriately heat treated to achieve the desired level of both flexibility and ductility.

As will be appreciated by those skilled in the art, the tabs 22, 24 and associated ribs 26a, 26b effectively define a ratchet of multiple locking positions, any of which may be selected by the vascular surgeon to accomodate various vein or tissue thicknesses without damaging the vein or tissue or otherwise further aggravating the trauma. With the forceps 10 locked on a vein, clamping a tear or opening in the vein, the vascular surgeon's hands are then free to perform other necessary functions, which may include the successive application of additional forceps 10.

Disengagement of the forceps 10 is facilitated by the flexibility of the pivotally connected stems 12, 14. Opposite lateral movement of the grips 18, 20 causes the ribs 26a, 26b to move apart to a point at which they no longer engage, allowing the grips 18, 20 to then be separated in such a manner as to open the jaws 12b, 14b and the clamp engaged at the end of the stems.

Those skilled in the art will appreciate that the invention provides not only a vascular clamp suitable for sequential side clamping of veins, but also provides in a single instrument the capability of performing both side and cross clamping. Indeed, it has been found that the instrument the capability of performing both side and cross clamping.

Thus it can be seen that the objects of the present invention have been satisfied by the structure presented above. While in accordance with the patent statutes only the best mode and preferred embodiment of the invention has been presented and described in detail, it is to be understood that the invention is not limited thereto or thereby. Accordingly, for an appreciation of the true scope and breadth of the invention references should be made to the following claims.

What is claimed is:

1. Medical forceps for vascular surgery, comprising:
   a first flexible stem;
   a second flexible stem pivotally connected to said first flexible stem;
   first and second grips respectively maintained at first ends of each of said first and second stems;
   first and second tips respectively maintained at second ends of each of said first and second stems and extending crosswise of said second ends of their respective first and second stems, said first tip having a first row of teeth thereon and said second tip having a pair of spaced apart rows of teeth thereon, said first row of teeth being received between said pair of rows of teeth to define a first vascular clamp, wherein said second ends of said first and second flexible stems define a pair of jaws having matingly aligned rows of teeth orthogonal to said rows of teeth of said first and second tips wherein each of said first and second tips extending laterally beyond the second end of its respective stem in two opposite directions; and
   a selectably actuatable and releasable lock interposed between said first and second flexible stems.

2. The medical forceps for vascular surgery according to claim 1, wherein said lock comprises a pair of tabs extending toward each other from said flexible stems and adjacent said grips.

3. The medical forceps for vascular surgery according to claim 2, wherein said tab is characterized by a plurality of ribs, said ribs being selectively lockingly interengageable with each other and imparting a force at said clamp as a function of said selective interengagement.

4. The medical forceps for vascular surgery according to claim 1, wherein said flexible stems are formed of heat treated 420 stainless steel.

5. The medical forceps for vascular surgery according to claim 1, wherein said second ends of said first and second flexible stems are normally bowed away from each other from a point where said first and second tips are first brought into contact with each other, said bow decreasing as force is applied to said grips beyond that necessary to bring said first and second tips into contact.

6. Medical forceps for vascular surgery, comprising:
   a first flexible stem;
   a second flexible stem pivotally connected to said first flexible stem, said first and second flexible stems respectively providing first and second jaws having matingly aligned rows of teeth that define a first vascular clamp for cross clamping; and
   first and second tips respectively maintained at distal ends of each of said first and second stems and extending crosswise of said distal ends, said first and second tips defining a second vascular clamp for sequential side clamping, said first tip having a first row of teeth thereon and said second tip having a pair of spaced apart rows of teeth thereon, said first row of teeth being received between said pair of spread apart rows of teeth in defining said vascular clamp and wherein each of said first and second tips extending laterally beyond the second end of its respective stem in two opposite directions.

7. The medical forceps for vascular surgery according to claim 6, wherein said distal first and second jaws are normally bowed away from each other from a point where said first and second tips are first brought into contact with each other to initially effect said second vascular clamp.

\* \* \* \* \*